(12) United States Patent
Hayzen et al.

(10) Patent No.: US 7,305,326 B2
(45) Date of Patent: Dec. 4, 2007

(54) ANALYSIS OF CONDITION MONITORING INFORMATION

(75) Inventors: Anthony J. Hayzen, Knoxville, TN (US); Raymond E. Garvey, Loudon, TN (US); Andrew Carey, Lenoir City, TN (US); Kenneth R. Piety, Knoxville, TN (US)

(73) Assignee: CSI Technology, Inc., Wilmington, DE (US)

( * ) Notice: Subject to any disclaimer, the term of this patent is extended or adjusted under 35 U.S.C. 154(b) by 0 days.

(21) Appl. No.: 11/345,457

(22) Filed: Feb. 1, 2006

(65) Prior Publication Data

US 2006/0161397 A1    Jul. 20, 2006

Related U.S. Application Data

(62) Division of application No. 10/921,557, filed on Aug. 19, 2004, now Pat. No. 7,027,959.

(60) Provisional application No. 60/497,117, filed on Aug. 21, 2003.

(51) Int. Cl.
    *G06F 11/30* (2006.01)
    *G06F 15/00* (2006.01)
    *G21C 17/00* (2006.01)

(52) U.S. Cl. .................................................. 702/185

(58) Field of Classification Search ................. 702/185
    See application file for complete search history.

(56) References Cited

U.S. PATENT DOCUMENTS

| 4,888,692 | A  | * | 12/1989 | Gupta et al. .................. 700/96 |
| 6,532,426 | B1 | * | 3/2003  | Hooks et al. .................. 702/81 |
| 6,651,012 | B1 | * | 11/2003 | Bechhoefer .................... 702/34 |
| 6,690,274 | B1 |   | 2/2004  | Bristol |

* cited by examiner

*Primary Examiner*—John Barlow
*Assistant Examiner*—Lisa Sievers
(74) *Attorney, Agent, or Firm*—Luedeka, Neely & Graham, P.C.

(57) ABSTRACT

A method is disclosed for acquisition and analysis of condition monitoring data. Alarm and alert limits are set to proper levels and information regarding the frequency and cause for alerts is collected. Analysis of the information may then be performed to provide a user with easily understandable representations of the system errors and suggested actions.

10 Claims, 6 Drawing Sheets

| Alarm Limit Set | # of Points | # of Samples | Sample Weeks | Alarm Weeks | Wear Weeks | Cont Weeks | Chem Weeks |
|---|---|---|---|---|---|---|---|
| 1 - Unknown / Other | 316 | 3454 | 14 | 15 | 19 | 21 | 20 |
| 2 - Motor/Unknown | 687 | 3897 | 23 | 26 | 38 | 31 | 37 |
| 9 - Turbine/Unknown | 101 | 1030 | 13 | 15 | 26 | 26 | 31 |
| 18 - Engine/Other/Natural Gas | 5 | 17 | 11 | 6 | | 13 | |
| 21 - Engine/Reciprocating/Gasoline | 20 | 51 | 5 | 6 | 63 | 6 | 26 |
| 22 - Engine/Reciprocating/Diesel | 42 | 892 | 10 | 9 | 23 | 18 | 14 |
| 26 - Pump/Unknown | 518 | 3505 | 19 | 20 | 36 | 32 | 33 |
| 35 - Air Handler (Fan)/Unknown | 188 | 1532 | 20 | 22 | 34 | 34 | 30 |
| 41 - Compressor/Unknown | 89 | 839 | 14 | 15 | 30 | 20 | 31 |
| 49 - Gear/Simple/Other | 761 | 4741 | 19 | 19 | 27 | 29 | 29 |
| 54 - Gear/Epicyclic/Other | 39 | 74 | 33 | 33 | 31 | 11 | |
| 59 - Roll Process/Unknown / Other | 2 | 38 | 11 | 11 | 50 | 29 | 41 |
| 63 - Centrifuge | 14 | 61 | 9 | 9 | | 7 | 11 |
| 64 - Machine Tool Spindle/Unknown / Q | 3 | 7 | 37 | 42 | 24 | 37 | 63 |
| 68 - Chipper / Crusher | 4 | 4 | | | | | |
| 69 - Agitator | 108 | 131 | 14 | 14 | 15 | 15 | |
| 71 - Chiller | 92 | 883 | 12 | 13 | 13 | 26 | 17 |
| 73 - Dynamometer | 15 | 47 | 14 | 14 | 7 | 16 | 16 |
| 76 - Pulverizer | 82 | 346 | 13 | 14 | 16 | 17 | 28 |
| 78 - Rotating Kiln | 60 | 189 | 19 | 19 | 26 | 25 | 31 |
| 79 - Hydraulic System/Unknown / Other | 149 | 649 | 14 | 16 | 18 | 32 | 32 |
| 82 - Central Lube System | 17 | 47 | 12 | 12 | 37 | 18 | 23 |
| 110 - Bearing Component | 30 | 112 | 14 | 15 | 20 | 18 | 18 |
| 140 - rolling element bearing | 13 | 56 | 18 | 21 | 14 | 23 | 19 |

Mean Time Between Alerts (MTBA) - CSI Default Oil AP Set

| Parameter | Units | Average | Minimum | Maximum | Count | Std Dev | Median | 1993 | 1994 |
|---|---|---|---|---|---|---|---|---|---|
| Visc 100C | Centistokes | 4.3700 | 0.0000 | 8.6200 | 9 | 3.4738 | 5.6000 | 8.4150 | |
| Chromium | Parts/Million | 0.0151 | 0.0000 | 1.0000 | 872 | 0.0695 | 0.0367 | 0.0251 | 0.0002 |
| Titanium | Parts/Million | 0.0066 | 0.0000 | 1.0000 | 533 | 0.0481 | 0.0379 | 0.0315 | 0.0000 |
| Silver | Parts/Million | 0.0146 | 0.0000 | 0.4350 | 460 | 0.0533 | 0.0367 | 0.0471 | 0.0000 |
| Nickel | Parts/Million | 0.0581 | 0.0000 | 3.0000 | 872 | 0.2216 | 0.0885 | 0.1070 | 0.0115 |
| Boron | Parts/Million | 0.3497 | 0.0000 | 16.1000 | 744 | 1.4734 | 0.1213 | 2.4850 | 0.5530 |
| Aluminum | Parts/Million | 0.2314 | 0.0000 | 83.0000 | 872 | 2.1656 | 0.3553 | 0.1643 | 0.0328 |
| Copper | Parts/Million | 2.9098 | 0.0000 | 43.8990 | 872 | 5.6079 | 1.4371 | 3.0593 | 7.7434 |
| Lead | Parts/Million | 1.5103 | 0.0000 | 34.0000 | 872 | 3.5815 | 2.2749 | 3.3206 | 3.3565 |
| Calcium | Parts/Million | 7.6816 | 0.0000 | 61.0000 | 752 | 13.5179 | 1.0678 | 1.0943 | 8.3718 |
| Silicon | Parts/Million | 3.5932 | 0.0000 | 321.2970 | 716 | 22.5233 | 1.4824 | 8.0154 | 26.2810 |
| Antimony | Parts/Million | 0.0042 | 0.0000 | 0.1980 | 257 | 0.0195 | 0.0000 | | 0.0000 |
| Tin | Parts/Million | 0.7076 | 0.0000 | 61.6980 | 872 | 2.7626 | 1.7323 | 1.8113 | 0.5360 |
| Barium | Parts/Million | 0.3609 | 0.0000 | 45.0000 | 529 | 2.0970 | 0.0000 | | 0.0000 |
| Zinc | Parts/Million | 52.1495 | 0.0000 | 464.0000 | 872 | 115.7264 | 3.5575 | 7.6079 | 22.8652 |
| Cadmium | Parts/Million | | | | | | | | |
| Phosphorus | Parts/Million | 46.7330 | 0.0000 | 313.0000 | 784 | 77.2413 | 3.2628 | 8.4927 | 23.8297 |
| Iron | Parts/Million | | | 260.0000 | 872 | 10052 | 30.1867 | 2.4638 | 1.6873 |
| Magnesium | Parts/Million | 0.6081 | 0.0000 | 12.0000 | 596 | 1.6877 | 0.0000 | | 2.6157 |
| Molybdenum | Parts/Million | 0.0776 | 0.0000 | 11.8500 | 596 | 0.6776 | 0.0000 | | 1.0500 |
| Potassium | Parts/Million | 0.0000 | 0.0000 | 0.0000 | 461 | 0.0000 | 0.0000 | | 0.0000 |
| Sodium | Parts/Million | 0.7754 | 0.0000 | 20.0000 | 529 | 1.6559 | 0.0000 | | 0.5706 |
| Vanadium | Parts/Million | 0.3080 | 0.0000 | 3.0000 | 481 | 0.5677 | 0.0000 | | 0.0000 |
| Manganese | Parts/Million | | | | | | | | |
| Chemical Idx | Index | 2.2690 | 0.0000 | 40.8500 | 299 | 4.5534 | 0.8000 | | |
| Cordem Idx | Index | 21.8119 | 0.0000 | 1362.2000 | 315 | 158.2653 | 0.0000 | | |
| Dielectric | Index | 2.2485 | 1.7820 | 2.6820 | 313 | 0.0856 | 2.2520 | | |
| Ferrous Idx | Index | 33.5191 | 0.0000 | 5005.0000 | 315 | 272.7463 | 0.0000 | | |
| % Water | Percentage | 0.1030 | 0.0000 | 10.2680 | 317 | 0.6042 | 0.0000 | | |
| Visc 40C | Centistokes | 50.7717 | 26.8200 | 105.0000 | 453 | 27.9161 | 30.0162 | 42.9638 | 41.9750 |

FIG. 1

| Mean Time Between Alerts (MTBA) - CSI Default Oil AP Set | | | | | | | |
|---|---|---|---|---|---|---|---|
| Alarm Limit Set | # of Points | # of Samples | Sample Weeks | Alarm Weeks | Wear Weeks | Cont Weeks | Chem Weeks |
| 1 - Unknown / Other | 316 | 3454 | 14 | 15 | 19 | 21 | 20 |
| 2 - Motor/Unknown | 687 | 3897 | 23 | 26 | 38 | 31 | 37 |
| 9 - Turbine/Unknown | 101 | 1030 | 13 | 15 | 26 | 26 | 31 |
| 18 - Engine/Other/Natural Gas | 5 | 17 | 11 | 6 | | 13 | |
| 21 - Engine/Reciprocating/Gasoline | 20 | 51 | 5 | 6 | 63 | 6 | 26 |
| 22 - Engine/Reciprocating/Diesel | 42 | 892 | 10 | 9 | 23 | 18 | 14 |
| 26 - Pump/Unknown | 519 | 3505 | 19 | 20 | 36 | 32 | 33 |
| 35 - Air Handler (Fan)/Unknown | 188 | 1532 | 20 | 22 | 34 | 34 | 30 |
| 41 - Compressor/Unknown | 89 | 839 | 14 | 15 | 30 | 20 | 31 |
| 49 - Gear/Simple/Other | 761 | 4741 | 18 | 19 | 27 | 28 | 29 |
| 54 - Gear/Epicyclic/Other | 39 | 74 | 33 | 33 | 31 | 11 | |
| 59 - Roll Process/Unknown / Other | 2 | 38 | 11 | 11 | 50 | 29 | 41 |
| 63 - Centrifuge | 14 | 61 | 8 | 9 | | 7 | 11 |
| 64 - Machine Tool Spindle/Unknown / O | 3 | 7 | 37 | 42 | 24 | 37 | 63 |
| 68 - Chipper / Crusher | 4 | 4 | | | | | |
| 69 - Agitator | 108 | 131 | 14 | 14 | 15 | 15 | |
| 71 - Chiller | 92 | 883 | 12 | 13 | 13 | 26 | 17 |
| 73 - Dynamometer | 15 | 47 | 14 | 14 | 7 | 16 | 16 |
| 76 - Pulverizer | 62 | 346 | 13 | 14 | 16 | 17 | 28 |
| 78 - Rotating Kiln | 60 | 189 | 19 | 19 | 28 | 25 | 31 |
| 79 - Hydraulic System/Unknown / Other | 149 | 649 | 14 | 16 | 18 | 32 | 32 |
| 82 - Central Lube System | 17 | 47 | 12 | 12 | 37 | 18 | 23 |
| 110 - Bearing Component | 30 | 112 | 14 | 15 | 20 | 18 | 18 |
| 140 - rolling element bearing | 13 | 56 | 18 | 21 | 14 | 23 | 19 |

FIG. 6

ANALYSIS OF CONDITION MONITORING INFORMATION

This is a utility patent application priority to Provisional Application Ser. No. 60/497,117 filed Aug. 21, 2003, the teachings of which are incorporated herein. This application is a divisional of application Ser. No. 10/921,557 filed Aug. 19, 2004 entitled Analysis of Condition Monitoring Information which issued as U.S. Pat. No. 7,027,959 on Apr. 11, 2006.

FIELD

This invention relates to the field of predictive maintenance systems. More particularly, this invention relates to methods of analyzing condition monitoring information.

BACKGROUND

Modern industrial plants typically utilize a predictive maintenance system or a condition monitoring system for monitoring and analyzing the condition of machines in the plant. Such machines typically include electric motors, pumps, fans, gearboxes, rotating shafts, presses, welders, mixers, furnaces, conveyor systems, and other equipment. The types of parameters collected from these machines vary depending upon the type of the machine, but the typical parameters include vibration, ultrasonic vibration, temperature, voltage, current, magnetic flux, thermal profiles, and alignment data. Condition monitoring systems generate a large amount of data that is challenging for even highly skilled operators to analyze. Often, plants utilize less skilled operators to obtain condition monitoring data and perform the initial analysis. Such lesser skilled operators have even more problems in understanding the data, and a missed problem may cause expensive down time for a plant. A method and device is needed which makes it easier for operators of all levels to understand and analyze monitoring data.

SUMMARY

The present invention simplifies the acquisition and analysis of condition monitoring data, and thereby makes it easier for an operator to understand the data. The invention may best be understood by an illustration starting with the collection of data. Typically, condition monitoring data is collected at intervals. An operator may collect the data from individual machines using portable equipment, or some of the data may be acquired using an on-line system that is continuously connected to the machines. As the data is collected, it is compared to alert levels and alarm levels that have been set for each measuring point. The alert levels and alarm levels are difficult to predetermine and initially are set almost arbitrarily based on the recommendations of the equipment manufacturer, or the policy of a particular plant. Typically, however, the recommendations of the equipment manufacturer are much too conservative and they cannot be used for a significant length of time. Also, it is usually impractical to set a policy within a plant establishing alert and alarm levels for every different measuring point for every different type of machine in the plant. Thus, the task of setting alert levels and alarm levels is actually part of the task of analyzing the data from the plant.

After the data has been collected for the first time in a particular plant or for a particular machine, the data is then analyzed to reset all of the alarm levels and alert levels for all of the measuring points on all of the machines. Assuming the entire plant had initial alert levels that were set based on the recommendations of manufacturers, it is likely that the entire plant is in an alert condition for the reasons explained in more detail hereinafter. Using the method of the present invention, the operator resets all of the alert levels and alarm levels based on an analysis of the condition monitoring data. The alert levels and alarm levels are set to place a given number of measurement points, or a given number of machines, or a given percentage of the measuring points or machines, into alert. For example, an operator may instruct the computer program to place 10% of the machines in the plant into alert. The computer program of the present invention then recalculates the alert levels for all measuring points of all machines in the plant, and resets the alert levels so that 10% of the machines are in an alert condition.

The above described method assumes that all machines in the plant are operational, but that the maintenance program needs to address problems on 10% of the machines. Thus, by implementing the above method, the worst 10% of the machines in the plant are identified for attention.

The method of the present invention analyzes the data to set alert levels and also analyzes the data to determine condition information regarding each machine and the machines as a whole. Such condition information would include an indication of the reliability of the overall plant and an indication of the reliability of the individual machines. In accordance with one aspect of the invention, a reliability index is calculated for each machine and for the factory as a whole. This reliability index gives the operator an immediate indication of whether a machine or a plant as a whole is reliable and if so to what extent it is reliable. The reliability index is preferably dependent upon both the alert level and the alarm level for each measuring point. Thus, it will be appreciated that setting the alert level and alarm level is part of the process of analyzing the data because setting those levels affects the interpretation of the data itself.

Also, the condition information generated by the program of the present invention includes an indication of the speed with which the reliability of a machine or a plant as a whole diminishes. Preferably, this information is produced in the form of a "Mean Time Between Alerts" (sometimes referred to as the "MTBA"), which is a measure of the time interval between alerts for a particular measuring point, a particular machine, or a particular group of machines. The "Mean Time Between Alerts" is then used by the program or the operator to determine and set the actual time interval between taking samples for each measuring point, machine, or group of machines. Preferably, the time interval between taking samples is set at one half the shortest MTBA in a group of measuring points of interest. For example, if a sampling interval is being set up for a particular machine having multiple measuring points, the sampling interval will be set at the "Mean Time Between Alerts" for the measuring point on the machine having the shortest MTBA.

The present invention also performs an analysis independent of alert levels and alarm levels to provide a check on the analysis that is dependent upon those levels. One such check performed by the present invention is an analysis that calculates an average measurement for each measurement point over time. Each time the average is calculated it is saved and compared to prior averages for the same the measuring point. Also, the averages are averaged, stored and compared to prior averages of averages for an entire machine, a group of machines, or an entire plant.

The average measurement at various measuring points may produce deceptive information because of extreme measurements that may be taken under unusual conditions that are far removed from a representative condition of a particular measuring point. To compensate for this possible defect, which might destroy the value of the averaging information, an average is taken for only a given percentile of the data, and the extreme readings for each measurement point are eliminated. For example, an average may be calculated for the 94th percentile, which means that the highest 6% of the measurements taken at a particular measurement point are eliminated, and an average is taken on the remaining 94% of the measurements at a measuring point. The percentile may be calculated based on a particular parameter that is monitored at a particular measuring point. For example, if a measuring point has 10 different parameters that are monitored, the 94 percentile will be determined for each parameter independently. However, in an alternative embodiment, the percentile will be calculated for a measurement point as a whole using a normalized parameter measurement for each parameter. In this alternate embodiment, all of the measurements taken during a particular sampling time will be ignored if the normalized average parameter measurement falls outside the percentile that was selected, such as 94%.

In accordance with another aspect of the invention, particle information is displayed and analyzed as part of the method of analyzing the condition monitoring data. Typically, the particles being counted are found in oil samples taken from machines. However, other sources of particle counts are found in most plants, such as samples of other types of fluid including liquid and gaseous. For example, it might be desirable to have a particle count for the air of a plant or the fuel used in a machine. One problem with particle counts is that the typical particle size of distribution information is almost meaningless, or at least somewhat deceptive, too many operators. To overcome this deficiency, the computer program of the present invention generates a new display that enables the operator to interpret the data more accurately and easily. In addition, the information is analyzed to suggest problems to the operator based on the particle count information. The display converts the original data to particle volume data based on an assumption that all particles are spherical. This assumption may not be true in all cases, but the information is still relatively accurate. That is, typically, the error for a small particle and the error for large particles will be similar and thus, the assumption concerning the spherical shape of the particle will cause proportionally the same error for both particle sizes.

After the particle volume is calculated, it is displayed in a graphical form with the particle volume shown on the vertical Y axis and the particle size shown on the horizontal X axis. This type of display is easier to understand by a typical operator because it will show a dramatic peak at a particle size that may be a problem. If only a count of the particle was displayed, the count of a large particle would be misleadingly low. Thus, the conversion to a volume of hypothetically spherical particles graphically and explicitly reveals potential problems to a user. In addition, the computer program calculates the volume of particles falling within the various particle size ranges of interest for the entire body of fluid under consideration. For example, if the fluid was taken from a 2 gallon oil tank of a vehicle, the volume of particles discovered in the sample would be extrapolated to the entire body of fluid. This extrapolation is typically displayed in a text form adjacent to the display of the curve. Finally, in addition to all of the above information, the computer program calculates the total volume of all of the particles and displays an indication of that total volume, such as a text display. It is easy for an operator to visualize a total amount of debris in a body of fluid, while it is difficult to understand and visualize data expressed in terms of parts per million.

In addition to generating a display of the calculated information, the computer program further analyzes the data to suggest potential problems. Such analysis would include a comparison of the current volumetric information to information contained in a library or knowledge base. By finding the closest fit to volumetric particle count distributions stored in memory, the computer program can suggest possible problems associated with a particular particle volume distribution. In particular, the program knowledge base may include a plurality of graphs showing particle size on the horizontal X axis and the total volume for each particle size on the Y axis. Each of these graphs may be typical of a particular type of problem associated with a particular type of machine, such as an electric motor or a pump. By finding the best fit between the stored curves and the subject curve, a potential problem is suggested by the program. In addition to finding one or more graphs in the knowledge base that match or almost match the current graph of interest, the computer program displays one or more curves and indicates the problem that is typically associated with the curve. Then, the user manually determines whether any of the selected stored curves correspond to the current curve of the interest. This technique not only allows the user to verify the best fit technique used by the computer program to identify a particular curve, it also allows the user to educate himself on the shape of curve is associated with particular problems.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIG. 1 is a screen display showing a tabular presentation of data corresponding to levels of contaminants in a fluid sample according to a preferred embodiment of the invention;

FIG. 6 is a screen display showing the mean time between alerts in a condition monitoring system according to a preferred embodiment of the invention.

DETAILED DESCRIPTION

Reliability Index

Figure 2:
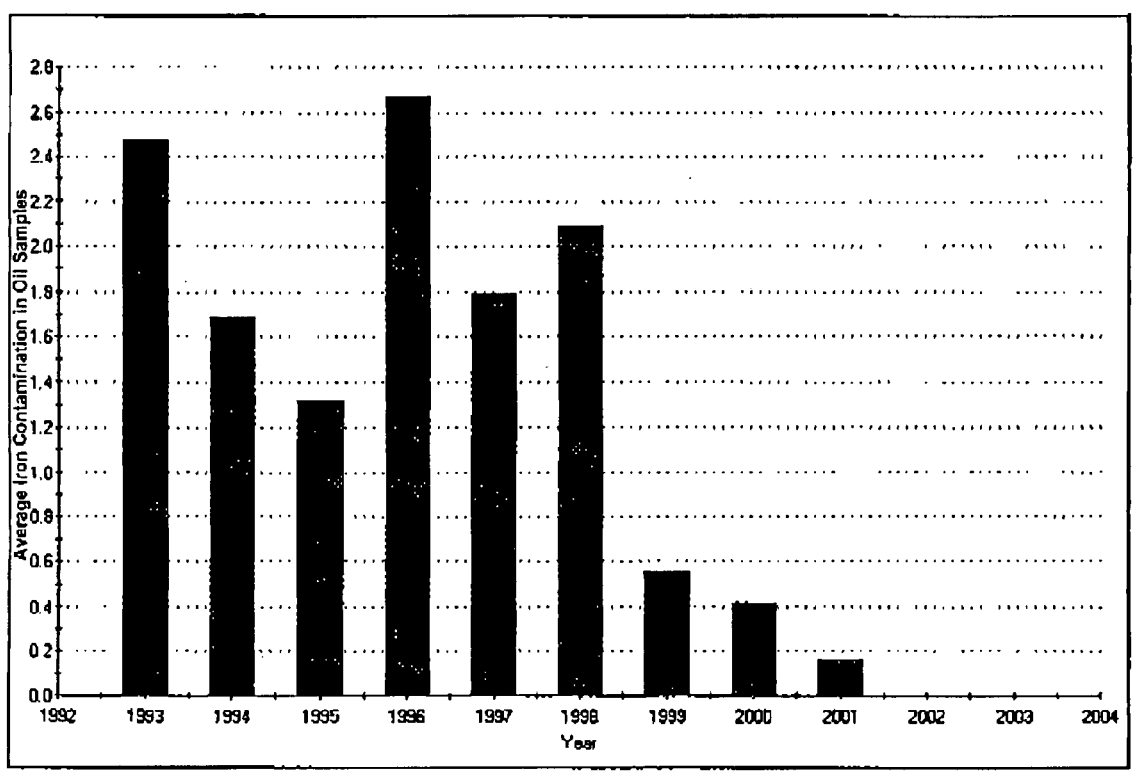
FIG. 2 is a screen display showing a graphical representation of the average amount of contaminant in a sample over a period of time according to a preferred embodiment of the invention.

In predictive maintenance systems, data may be collected using a wide variety of machines and stored in a computer database, such a database available under the trade name RBM from Computational Systems Inc. of Knoxville, Tenn. Such data may include almost any parameter that can be measured on a machine. For example, the data may include data related to vibration, ultrasonic vibration, temperature, thermal properties, oil properties, voltage, current, magnetic flux, alignment of machines, and other operational information. Typically, the data collection systems have cooperating software that enables the user to assign an alert level and an alarm level for each parameter that is measured. For example, in the case of vibration, the user may specify an alert level and an alarm level based on the overall magnitude of all vibration. Of course, the alarm level of vibration would be higher than the alert level. More complicated alarm and alert levels may also be established. For example, alert and alarm levels may be specified for particular frequency bands of interest. Again, for a particular frequency band, the alert level is normally lower than the alarm level.

One of the challenges facing predictive maintenance personnel is to quickly analyze the predictive maintenance data and make sound decisions based on that data. Providing a reference value described herein as a "reliability index" in accordance with the invention facilitates this task and enables the engineer to more quickly evaluate, understand and communicate the status of machines that are being monitored.

In accordance with the present invention and by use of a microprocessor-based system having an appropriately configured computer program, a reliability index is preferably calculated for each machine, for each machine group, and for an entire plant. The reliability index is calculated based on all or selected parameters collected on a group of machines. The reliability index is preferably selected to be a function of the selected data and is a representation of a comparison between the measured parameters and at least one of the alert limits and the alarm limits. For example, in one embodiment the comparison could be made by simply subtracting the current measured value from the alarm limit value. In such case, a larger number would indicate a greater reliability. In another embodiment, the comparison may be made by multiplying the current value by the alarm limit. Again, higher numbers would indicate more reliable machines. The numbers generated by subtracting or multiplying in the manner suggested above would create meaningful numbers, but those numbers may vary greatly from machine to machine. Thus, the numbers generated by the aforementioned multiplying or subtracting are preferably normalized so that they fall within the same range and the numbers are more meaningful because the normalized numbers are comparable between machines.

For example, in a preferred embodiment, a comparison is generated by dividing the alert level by the current measured value of a particular parameter. Then, the ratio is preferably normalized to a number falling between 100 and −100. For example, in this embodiment, the algorithm uses a severity index (1-100) of each technology (Vibration, Oil, Thermography, Motor etc.) in the RBM database and combines this severity index with an equivalent index (1-100) of non-alert data to create an overall reliability index for equipment and plants.

In this manner, a reliability index for a single or a group of machines for each interval in a selected time period may be obtained. The range of values for the reliability index is preferably selected to range from about −100 for the worst machine to about +100 for the most reliable machine. A machine which is at its alert level is preferably assigned a value of 0.

The reliability index for each machine may be obtained as follows:

Using the last data in each interval, a ratio is generated by dividing the alert limit by the current value of a particular parameter measured on a machine. This ratio is then normalized by assigning it a value between −100 and +100. In this particular embodiment, the normalization process assigns some reliability values that are dependent upon only the ratio, but some reliability values may preferably be assigned based on both the ratio and the alarm level. The positive reliability values are preferably assigned based on the ratio and the negative reliability values are preferably assigned based upon the ratios and the alarm level.

For the purpose of example only, the following charts show preferred values for reliability index values for the indicated ratios. Reliability index values are preferably linearly interpolated in the ranges below. For example, if the ratio of the alert limit/the current value equals 1.5, then the reliability index value is preferably linearly interpolated to be half way between zero and 40. Thus, the reliability index value would be 20 for a ratio of 1.5.

Positive Reliability Index Values

| | |
|---|---|
| 0 to 40 | for Ratio >= 1.0 and <= 2.0 |
| 41 to 70 | for Ratio > 2.0 and <= 4.0 |
| 71 to 100 | for Ratio > 4.0 and <= 15.0 |
| 100 | for Ratio > 15.0 |

Negative Reliability Index Values

| | |
|---|---|
| −1 to −20 | for Current Value >= Alert and <= 0.5*Alarm |
| −21 to −40 | for Current Value > 0.5*Alarm and <= Alarm |
| −41 to −70 | for Current Value > Alarm and <= 4.0*Alarm |
| −71 to −100 | for Current Value > 4.0*Alarm and <= 12.0*Alarm |
| −100 | for Current Value > 12.0*Alarm |

In the preferred embodiment, all parameters for each measurement point are tested against their alert/alarm levels and the worst (lowest value equals most unreliable) is retained for that measurement point. For example, one measurement point on a machine may have three alert levels for vibration assigned for three different frequencies. In creating the reliability index, it is preferred to store only the data for the frequency having the lowest reliability index value. Preferably, if more than one parameter is in alarm, one point for each alarmed parameter is subtracted from the metric up to a maximum of five points.

The reliability index for the machine for each interval is preferably selected to be the lowest score for any of the measurement points tested on the machine. If more than one measurement point is in alarm, one point for each additional measurement point in alarm is subtracted from the index up to a maximum of five points. The exact penalty for multiple measurement points in alarm may be adjusted but a machine is typically considered to be less reliable if more points are in alarm.

In the preferred embodiment, the reliability index is also preferably aged, preferably by adjusting, as by lowering its value as a function of time. The reliability index for each machine may be aged by the amount the user specifies for a reliable machine or for an unreliable machine on a monthly basis. This is preferably defaulted to 5-10 points per month. Aging may also be performed at the measurement point level instead of the machine level and done on the basis of the surveillance interval for that point. However, the aging for the machine may be easier for a user to understand and will produce a similar effect since the reliability index is the lowest (most unreliable) index score for any point. Aging at the measurement point level may result in some variation if the worst points were missed but other reliable points (not in alarm) were collected. Aging advantageously provides the ability to penalize the program for machines for which data has not been collected during the interval. In this regard, it is preferred to assume that a machine's reliability remains the same or gets worse with time, but does not improve. Furthermore, the plant is in a worse (less protected) state for a machine whose current condition is not known. It is also preferred to apply less penalty to a reliable machine versus an unreliable machine whose current condition has not been assessed in the prescribed interval. Therefore, the aging penalty may be a function of time and an inverse function of the current reliability index.

For example, the aging penalty may be calculated by multiplying 8 points times the number of months since the last time data was taken to produce a preliminary aging penalty. The current reliability index divided by 20 is then subtracted from the aging penalty to produce the final aging penalty. For example, if the data has not been collected from the machine for two months and the reliability index is 50, then the preliminary aging penalty is determined to be eight times two months, which equals 16. The current reliability index is then divided by 20, which equals 2.5 (50/20=2.5). Thus, 2.5 would be subtracted from the preliminary aging penalty and the final aging penalty would be 13.5 (16−2.5=13.5). This example is intended for illustration purposes only and the magnitude of the numbers for the aging penalty may or may not make sense depending upon the application. In this regard, the aging penalty is preferably adjusted to reflect how quickly a particular type of machine deteriorates in reliability over time and the degree to which a very reliable machine will resist deterioration in reliability.

The reliability index for a set of machines is selected to be the average of the reliability index for each of the machines for each interval of time. In order to get values for the overall reliability index that can be trended over time, it is desirable for the set of machines in each interval to be constant. Accordingly, it is preferred to age the value for a machine rather than omitting one not monitored/measured during that interval.

A second feature of the method is the generation by the computer program controlled microprocessor of a report providing an ordered list of the most unreliable machines based on the latest interval. This report also preferably shows individual reliability trends of each machine over time. Preferably, this trending is illustrated by displaying a graph of the reliability index of a machine over time. However, this trend may also be displayed or represented by a single number such as a positive number to represent a machine that is increasing in reliability over time and a negative number to represent a machine that is decreasing over time. The size of the number, both positive and negative, may be used to evaluate the magnitude of the increase or decrease in reliability over time. This feature may also be expanded to show an ordered list that includes reliable machines in addition to machines that are considered unreliable. This information may be particularly important to a facility that is changing out or performing maintenance on a certain percentage of the equipment each outage and desires a list of the best candidates to service.

Reliability Percentile Metrics

In analyzing predictive maintenance data, one goal is to analyze the effectiveness of a particular predictive maintenance program. For example, if a predictive maintenance program has been established to monitor oil in machines, the data acquired by the predictive maintenance program preferably indicates whether the program has been effective or excessively effective. One way to determine such effectiveness is to measure the average value of a condition monitoring parameter such as the amount of iron detected in the oil over a period of time. If the condition monitoring program is effective in improving plant reliability, then one would expect the average value for either a specific piece of equipment or a group of equipment to decline over time. This would be one way to evaluate the effectiveness of the program.

It has been observed that sometimes the average value is not necessarily reliable due to distortions from exceptional values. This problem can be overcome by using different measures such as the 90, 94, 97 or 99 percentile. The 90th percentile of a particular set of data would include all of the data except the top 10% of the measurements. Thus, 90% of the data may be retained and 10% of the worst data would be ignored. In the case of an iron parameter, where the amount of iron is measured in a sample of oil, the measurements of iron may be ordered according to the quantity of iron in the oil, the 10% of the samples having the most iron would be ignored when calculating the average iron in a sample.

The method of the present invention is preferably implemented to cooperate with a computerized data collection system operating software under the trade name RBM and available from Computational Systems, Inc. That is, the preferred methodology may be achieved by providing additional computer program(s) to desirably interact with the data obtained by the data collection system. In this implementation, the screen display in FIG. 1 shows a typical oil sample showing the various contaminants that may be found in oil and showing a display which includes yearly averages. In FIG. 1, an average has been chosen to include all samples, but the screen shows the selection boxes (circles) for selecting four different percentile groups for which an average calculation may be made.

The calculation of a yearly average of a particular parameter may be selected by clicking on either "Average, 90%, 94%, 97%, or 99%". If "average" is selected, the average amount of each parameter is calculated for each year using all samples available for the particular year. If "90%" is selected by clicking in the circle shown in FIG. 1, then an average is calculated for each year using only the $90^{th}$ percentile of the data. In other words, the largest 10% of values are preferably ignored. Likewise, if the user clicks the circle next to "94%", the computer program calculates an average for each parameter based on the $94^{th}$ percentile, ignoring the 6% of the data having the largest of values for each parameter.

The percentile averages may be determined on a parameter by parameter basis. Thus, when the program is calculating an average for the $94^{th}$ percentile, it may use a different set of samples for each parameter. For example, it is unlikely that the same set of samples will include both the most iron and the most sodium. Thus, when the 94th percentile for iron is calculated, the computer program will generally be eliminating the samples having the highest value of measured iron. Likewise, when the 94th percentile for sodium is selected, the computer program will ignore the samples having the highest value for sodium. It is likely that the samples considered in calculating the 94$^{th}$ percentile average for iron will be different from the samples used in the calculation for sodium.

In an alternate embodiment, the percentiles are calculated based on samples, not individual parameters. In this alternate embodiment, when a percentile is calculated, the same set of samples is used to calculate the percentile. For example, if a user is calculating a 94th percentile, the program will first identify a set of samples that falls into the 94th percentile based upon a normalized measurement of all parameters. For each parameter, the highest measurement is considered a 1 and the lowest measurement is considered a 0. All of the measurements between the highest and lowest are linearly interpolated between zero and one. Then, these normalized measurements are used to select the 94th percentile. For example, all of the normalized measurements may be added together and then divided by the total number of parameters measured in the particular sample to generate a single normalized measurement for each oil sample. Then, this single normalized measurement is used to identify the oil samples that should be retained in the 94th percentile. Finally, the original oil samples that are in the 94$^{th}$ percentile are used to calculate the 94th percentile average for each parameter, such as iron.

If the user wishes to consider other percentile groups, such as the 97th or the 99th percentile, then the circles in FIG. 1 beside either 97% or 99% may be selected, and the computer program calculates the averages for each parameter within the selected percentile in the same manner as discussed above.

The systems and methods of the present invention also enable graphical display of the calculation of averages or percentile averages as discussed above. After calculating the various types of averages over time for specific parameters, they can then be plotted over time as shown in FIG. 2 to give a graphical representation. Typically the parameters that are of interest fall into the wear and contamination categories for oil analysis data. Similar type parameters can also be used for other technologies such as vibration.

Analysis of Particles in Oil

In the predictive maintenance systems, the analysis of oil is important to determine the current condition and predict the future condition of machines. One of the tools used to analyze oil is a particle count size distribution. However, despite the usefulness of the information provided by a particle count and size analysis of oil, such analysis is often overlooked or intentionally neglected because of the difficulty of using the information. Instead, techniques such as a spectrograph are used that simply tell the user about the nature of the contamination, but spectrographs do not provide information about particle counts or sizes, and in fact they may not detect certain large particles because insufficient energy is provided to vaporize the particles. Large particles that would defeat some spectrographs are often indicators of serious problems in a machine.

The present invention advantageously provides an automated analysis of a particle count and size distribution that includes a display technique designed to quickly convey important information to the user concerning problems or potential problems in a machine.

A traditional manner of providing particle size and count information is a chart where the particle size is listed along the left-hand column and the count of particles is listed in a right hand column. For each particle size in the left-hand column, the right-hand column indicates a count for that size particle.

Figure 3:
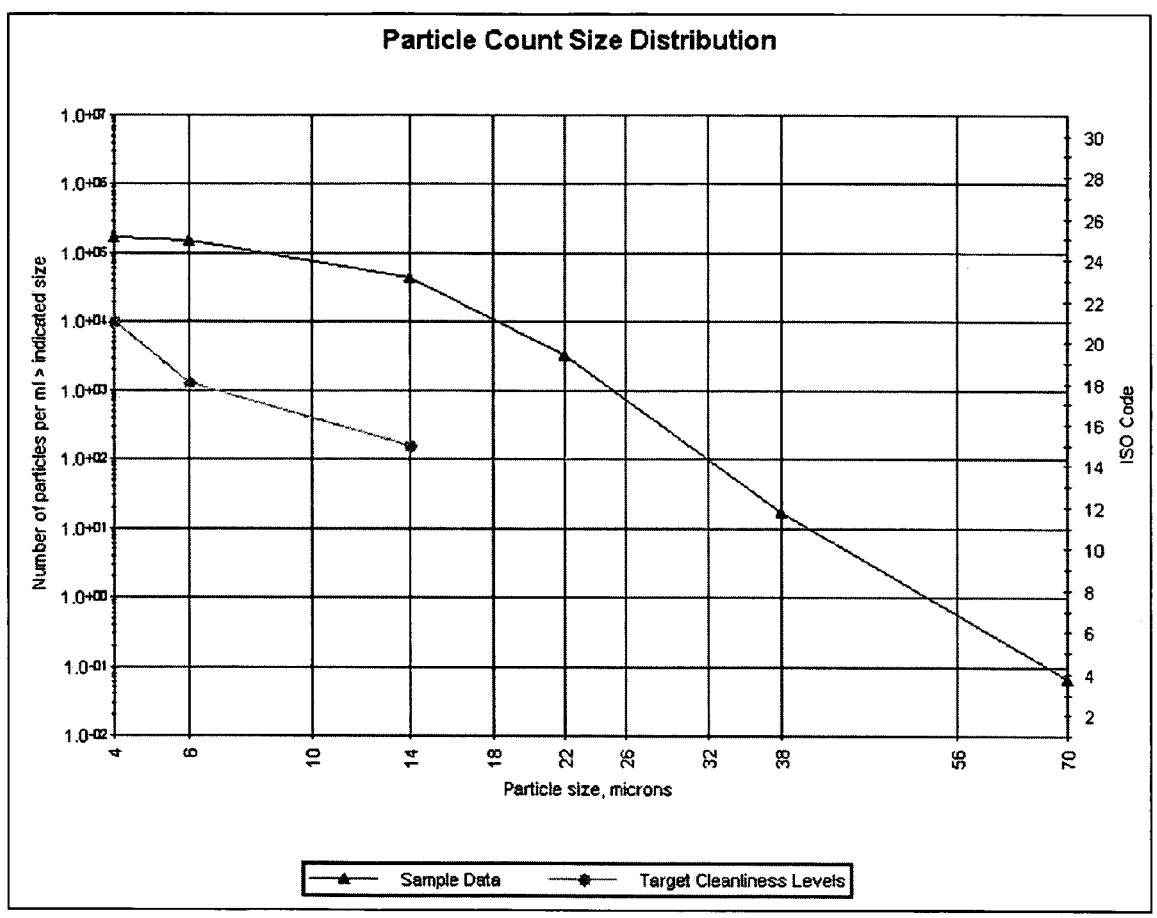
FIG. 3 is a screen display showing a prior art particle count size distribution.

Another traditional technique for displaying particle size and count information is to display a chart such as that shown in FIG. 3 in which a curve is displayed on a two axis chart. The vertical Y axis indicates the number of particles and the horizontal X axis indicates the size of the particles. Thus, the curve illustrates a distribution curve representing the number of particles that were counted at each particular size of particles.

One problem with the chart shown in FIG. 3 is that it does not tend to identify problems. Where the size of particles is small, the standard chart will display a very large number, but that large number may not be indicative of a problem. Very small particles may be huge in numbers but represent a very small amount of material. Likewise, very large particles may have a small count but represent a relatively large volume of material as compared to the small particles. Thus, the standard size distribution chart may actually provide misleading information to someone who is not very familiar with the meaning of such chart. To overcome this problem, a method of this invention enables generation of a chart such as shown in FIG. 4.

The Particle Count Size Distribution plot shown in FIG. 3 is the standard method of graphically displaying particle counts with actual data at the measure sizes, typically 4, 6, 14, 22, 38 and 70 micron sizes using the ISO 11171 standard. If particle size was measured using the old ISO 4406 standard, then the particle counts must be converted to the new sizes to ensure accurate conversion to particle volume.

Figure 4:
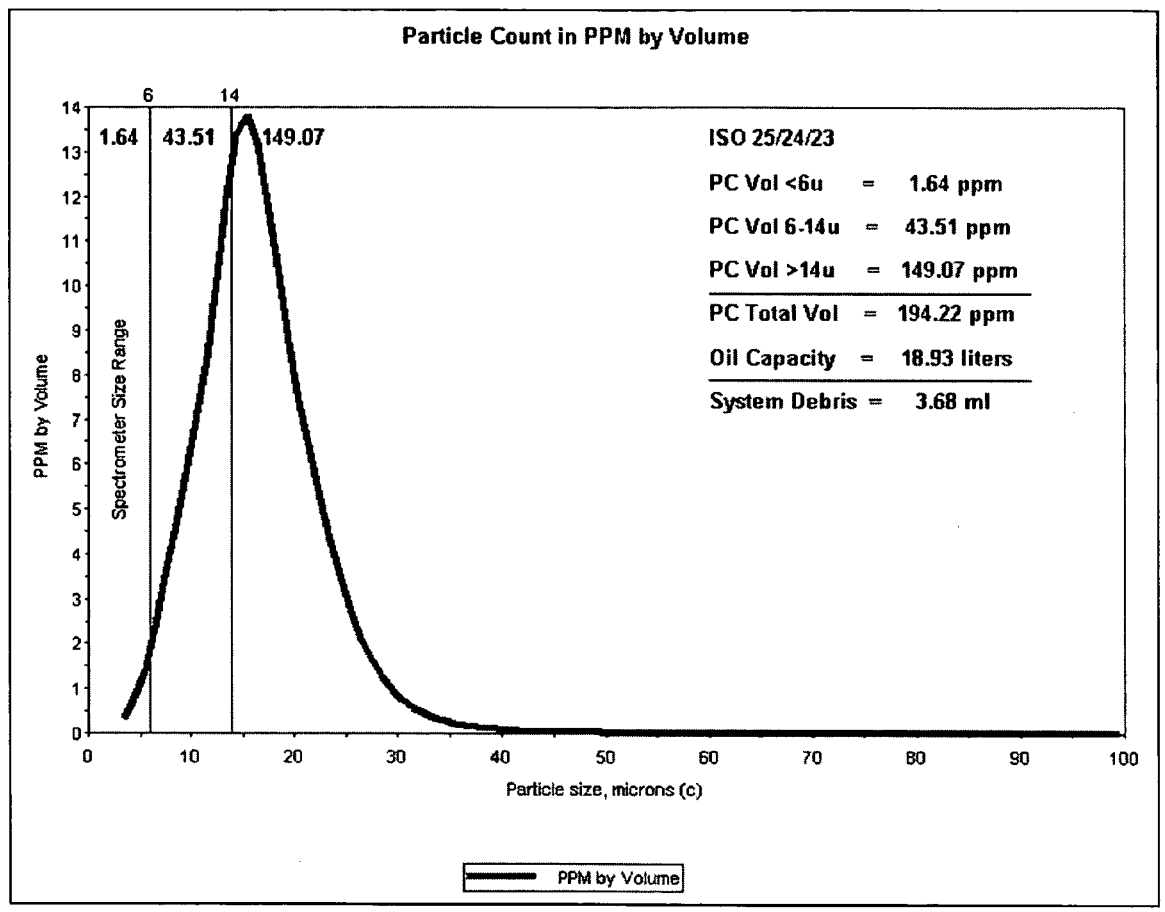
FIG. 4 is a screen display showing a representation of the relation between particle volume and particle size in a fluid sample according to a preferred embodiment of the invention.

To convert the data to the chart shown in FIG. 4, it is assumed that the particles are spherical so that one can use the standard formula for the volume of a sphere to then calculate the total volume concentration of particles at each size given the particle count distribution at each size as shown in FIG. 3. This gives a plot of particle volume concentration versus size as shown in FIG. 4.

In addition to calculating and displaying the particle count in ppm by volume, the particle volume size distribution plot of FIG. 4 is used to calculate the total volume of particles measured as "Particles Per Million" (PPM), or any other way of reporting volume of particles, present in the oil or any other fluid. The total volume of particles may also be reported for any intermediate size distribution as shown in FIG. 4. The data can be fitted to a log normal distribution curve, or integrated by parts over the range.

Given the concentration of particle per unit volume of fluid, (PPM) this value is multiplied by the total volume of oil (fluid) being used to give the total volume of particles present in the system as shown by "System Debris" above. In other words the total amount of trash in a machine may be calculated, for example. A machine operator can easily visualize a total volume amount of trash in an engine and understand the consequences of that trash. Thus, the operator is more likely to understand and act upon the information.

In the display shown in FIG. 4, it is easy to see that the volume of the debris in the fluid peaks dramatically at 16 microns. Thus, the volume display in and of itself tends to suggest the nature of the problem associated with the test. In other words, it shows that something is causing a huge volume of 16 micron particles, and 16 micron particles are typically associated with a particular type of problem. In addition to displaying the curve, as shown in FIG. 4, the present invention calculates and displays the total amount of system debris in ml, the total oil capacity of the machine and the total volume of the particles counted in parts per million. Again, conversion of the parts per million data to a total amount of system debris enables quick understanding of the severity of the problem. It is easy to visualize a 3.68 ml of debris. It is difficult to visualize 194.22 parts per million of debris.

In addition, for the more skilled users, the chart in FIG. 4 displays in parts per million the volume of particles having a size of less than six microns, the volume of particles having a size between six and fourteen microns, and the volume of particles whose size exceeds fourteen microns.

After displaying the information as discussed above, additional information may be requested by the operator. For example, the operator may request an analysis of the particle count distribution. A knowledge base associates particular types of problems with a particular particle count distribution. In one embodiment, the knowledge base will include a number of stored curves, and each of the stored curves is associated with a particular type of problem. The current particle count curve is normalized and compared to the stored curves in the knowledge base. Curves may be identified within the knowledge base that most resemble the curve being analyzed. Preferably this is done using a best fit technique. A report may be provided to the user indicating one or more possible problems and a confidence factor indicating how close the stored curve matched or fit the subject curve under consideration. Thus, the confidence factor may be considered by the user when evaluating the suggestion. If only one potential problem has a high confidence factor, the suggestion is probably correct. If several problems have a roughly equal confidence factor, the machine may have both problems or neither problem, and the user must exercise more caution with the suggestions.

In accordance with a preferred embodiment, a value corresponds to the total mass of particles present in an oil sample by estimating the average density of the particles present and multiplying that density by the total volume of the particles present. This may be facilitated by accessing a knowledge base that correlates size distribution curves to the type of particles present as well as the particle shape and material. For example, one type of size distribution curve would indicate that large particles were iron particles, and thus the mass of the particles would be calculated based on the assumption that the large particles were iron. Other distribution curves would indicate that water was present in the oil, and the calculation of water mass would be based on the characteristics of water. Accordingly, an estimate of the mass and type of particles may be obtained and a confidence factor may be provided indicating how well the subject curve had characteristics that could be matched to curves in the knowledge base.

Alarm Limit Analysis and Correction

In the field of predictive maintenance it is sometimes difficult to set reliable and reasonable alarm limits for various parameters that are measured during a predictive maintenance program. If a large number of parameters are being measured, the job of setting alarm limits becomes more difficult because of the cumulative effect of multiple alarms based on multiple parameters. For example, if each measured parameter is set at a level that will cause an alarm in 10 percent of the machines in a plant, and the 300 parameters are measured on each machine, it is highly likely that every machine or almost every machine would go into alarm. This phenomenon results from the fact that the alarms caused by each parameter do not correlate well with each other. In other words, an alarm limit reached in one machine based on one parameter does not predict that any other parameter of that machine will also go into alarm. Thus, the alarm limits are reached on the various machines in an almost random fashion. If one assumes a random distribution of alarms in the above example, then each machine in the plant should have about 30 parameters in alarm. (300 parameters*10% in alarm). This is an extreme example designed to illustrate the point.

A less extreme version of this problem applies to any type of condition monitoring method or technology. The problem is that multiple parameter alarms have a cumulative effect on severity that is different from a single parameter in that they almost always cause more samples to be in alarm than any individual parameter. An exception to this is if all parameters in alarm go into alarm at the same time on the same machines, which is highly unlikely. Therefore, if an individual parameter causes only 10% of the sample data to go into an alarm state, then multiple parameter alarms on the same sample data will cause more than 10% of the samples to be in alarm. It would not be unrealistic for this number to be as high as 90% of the samples. This is because the correlation of alarming between the various parameters is low.

Figure 5:
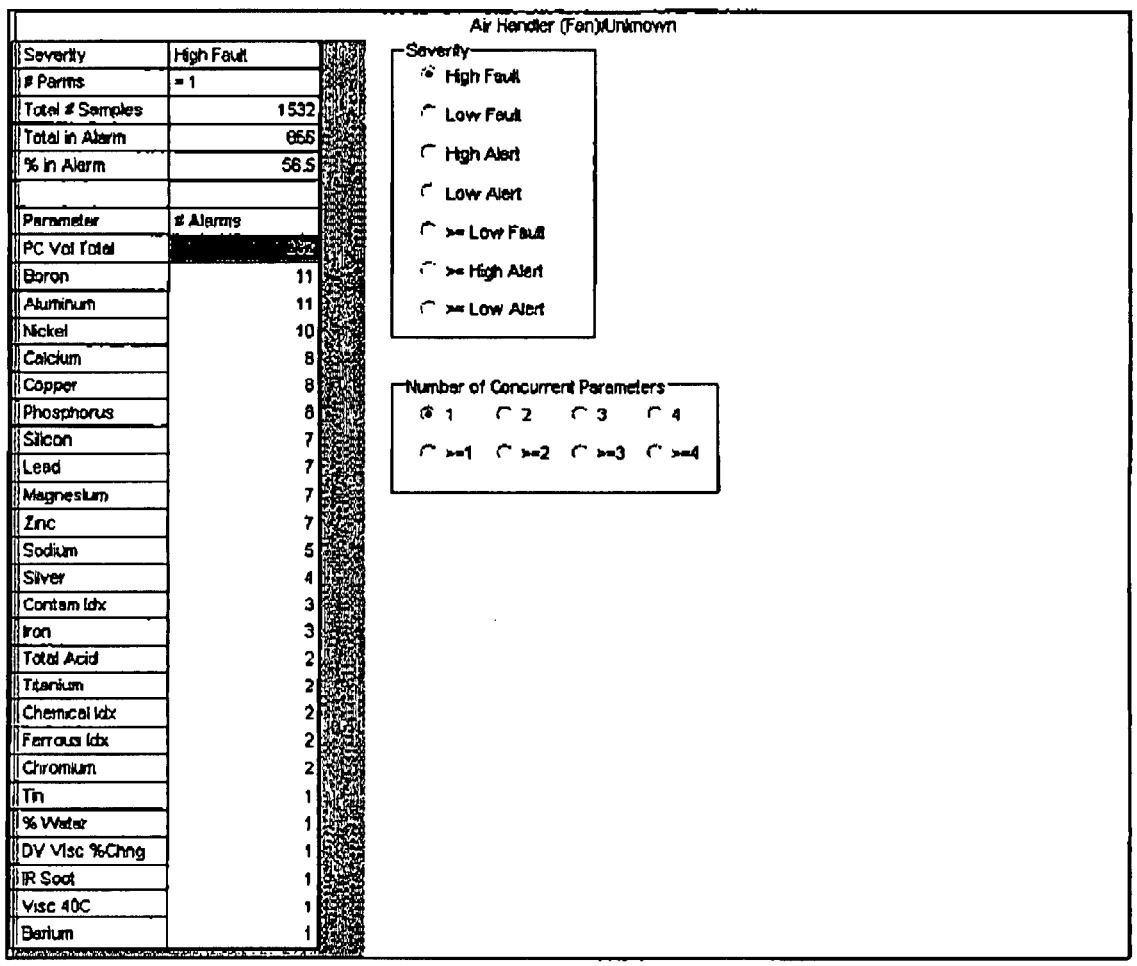
FIG. 5 is a screen display showing alarm information for a system of machines according to a preferred embodiment of the invention.

The present invention addresses this problem by selecting alarm limits for each parameter with consideration for the cumulative effect of the alarm limits for all of the parameters. The first step in this method is to select the alarm limits for each measured parameter in a conservative fashion and then analyze the data to determine the percentage of machines in an alarm state. This first step is illustrated in FIG. 5, which shows the number of alarms caused by each parameter and it shows the percentage of machines (samples) that are in an alarm condition. In this example, 56.5 percent of the machines (samples) are in an alarm condition. One parameter is determined to be at fault based on its excessive alarm condition. The "PC Vol Total" parameter is causing too many samples (232) to go into alarm and is, therefore, adjusted to be less sensitive. The next highest parameter is boron which produces 11 samples to go into alarm. Comparing just the two highest parameters, it is determined that the "PC Vol Total" parameter is creating excessive numbers of alarm conditions. Again, this is an extreme example designed to illustrate the point that displaying the number of alarms caused by each parameter facilitates the identification of problems in the alarm levels set for one or more of the parameters.

The correction of the alarm levels may be accomplished manually or automatically. In the automatic mode, the user sets an absolute number of samples or the percentage of overall samples that the user wishes to place in alarm condition. For example, the user may set the overall alarm condition to be 10% by typing 10 into the "% in Alarm" field, which identifies the percentage of samples in alarm. Alternatively, the user may enter an absolute number into the "Total in Alarm" field, which indicates the number of samples that he wishes to be in alarm. Then, the computer automatically calculates the alarm settings for the various parameters that will place the desired number (or the desired percentage) of the samples into alarm. Preferably, the computer will reduce the alarm levels of the parameters producing the highest number of alarms until the desired overall number (or percentage) of alarms has been achieved.

In the example below, the computer will reduce the alarm level on the parameter "PC Vol total" until a desired overall alarm condition is achieved or until the "PC Vol total" parameter is producing the same number of alarms as the next lowest parameter. In this case, the alarm level of "PC Vol total" is reduced until it produces 11 alarms, which is the same number of alarm levels as caused by boron and aluminum. If the overall alarm level has not reached a desired percentage or number, the computer will reduce the alarm levels of the parameters producing the highest number of alarms until an overall desired percentage alarm level (or number of alarms) is reached (such as 10%), or until the top alarm producing parameters produce the same number of alarms as the next highest parameter. In this case, aluminum and boron are tied for the second highest alarm level producing parameter, and, thus both of these parameters will have their alarm levels reduced until they produce 10 alarms each, which is equal to the number of alarms produced by a copper, calcium and phosphorus. If the total alarm level has still not reached a desired percentage of the samples, the top six parameters will have their alarm levels reduced. The computer will continue to reduce alarm levels on the top parameters until the overall alarm level reaches the desired setting, such as 10 percent of the samples in alarm.

The preferred embodiment of the invention also has a feature whereby the user may "protect" one or more parameters from having its alarm level changed. When such parameters are identified by the user as protected, the automatic reduction of alarm levels will be performed without changing the alarm levels of the protected parameters. Thus, a user may select certain protected parameters, manually set the alarm level of those protected parameters, and then instruct the computer to automatically lower the alarm levels of the remaining unprotected parameters in the manner described above until the overall alarm level reaches a desired percentage.

Finally, the method of the present invention may be implemented in a pseudo manual manner. In such case, the user will select a number of parameters and change the alarm level for the selected parameters. Each time the user changes an alarm level, the computer will recalculate the total number of samples that are in an alarm condition and display the number samples in alarm and the percentage of samples in alarm. Thus, as the user changes alarm levels, the computer will display the effect achieved and thereby facilitate the eventual arrival at a desirable overall alarm level.

In summary, it is important to understand the cumulative effect of alarm limits for multiple parameters when setting alarm limits, and the method described above measures the overall percentage of samples in alarm and shows how many of the samples were put into alarm by each parameter. This information is then used to evaluate the alarm limits for each parameter and adjust them accordingly so the cumulative effect of multiple alarms does not cause an excessive number of samples to go into an alarm state. This adjustment process may be done automatically, partially automatically, or pseudo manually.

The method of the invention can be applied to any type of data that has more than one alarm type or parameter and does not depend on how the original alarm level was set. The method also advantageously evaluates the effect of these multiple alarm levels on a given set of sample data enabling the user to establish reliable alarm limits based on their specific data. In this manner, the user may ensure that a desired percentage of samples (machines) are in an alarm condition at all times. Thus, the invention advantageously facilitates identification of the machines in a group of machines that are in most need of preventative maintenance measures.

Analyzing Alert Data

One of the important measures of equipment reliability is "Mean Time between Failures." This information is typically not easily made available to condition monitoring systems and, therefore, it is difficult to measure the benefit of such a program. To solve this problem, the method of the present invention analyzes alert data, which is easily accessible to condition monitoring systems, to generate a measurement of the effectiveness of the program. Preferably, the method of the present invention is implemented to generate a measure called "Mean Time between Alerts (MTBA)." Alerts are an integral part of a condition monitoring system and alerts are closely related to potential failures. Therefore, by measuring and displaying MTBA over different time periods, one can gain a measure of the effectiveness of a condition monitoring program. The MTBA can also be used to establish sampling intervals to ensure that equipment problems are not missed. Preferably, the sampling interval is a percentage of the MTBA, preferably 50%.

This MTBA can also be broken down into different types of alerts such as Wear, Contamination, or Chemistry in an oil monitoring program. These categories are provided as examples of the many different categories that may be selected depending upon the monitored conditions. For example, parameters such as vibration, ultrasonic vibration, voltage, current, magnetic flux, temperature, thermal profiles, and the like may be used to generate predictive maintenance data.

Alert limits and the alarm limits are then set for the chosen parameters as discussed herein. Preferably, alert levels are set so that a desired percentage of machines in a plant are in an alert condition at any time. For example, alert levels may be set to nominally place into an alert condition 10 percent of all machines in a plant. Predictive maintenance data is typically collected in a cyclical fashion whereby the data is collected from the machines at set intervals. Those intervals are often set arbitrarily based on the intuition of the predictive maintenance engineer. At least initially, it may be necessary to arbitrarily set the intervals between samples. However, one objective of this method is to assist the predictive maintenance engineer in establishing intervals between samples of predictive maintenance data. Each time that the data is collected, the information is dated and an alert condition is either present or not present. Thus, the time of each alert condition is known and stored in the predictive maintenance data. In addition, alert conditions are attributed to a particular type of parameter and a particular type or category of alert condition. As mentioned above, alert conditions of oil parameters are categorized into conditions related to wear, contamination, or chemistry. For example, the presence of iron in oil is an indication of wear.

In addition to setting alert levels of predictive maintenance, engineers will also set alarm levels for various machines. When an alarm is detected, all information pertinent to the alarm is stored. Such information would include the date on which the alarm was detected, the parameter generating the alarm, and the category of the alarm. In the case of oil, an alarm condition may be categorized as contamination, for example.

Using the computer display shown in FIG. 6 as an example, the method of the present invention may be described in greater detail. FIG. 6 displays information derived from a predictive maintenance database. In this example, the parameters that have been measured relate to oil, but other parameters could be used as well.

Operating on the predictive maintenance data that is normally acquired, the method of the present invention calculates the number of weeks between each alert condition for each machine in a particular grouping such as the plant. Then, for all of the data that has been acquired, the method calculates a mean interval between alerts for each machine. This information is displayed under the heading "Sample weeks" in the table in FIG. 6. Thus, for the No. 18 engine, the mean time interval between alerts was 11 weeks. For the No. 35 error handler, the mean time between alerts was 20 weeks. In addition to calculating the mean time between alerts, the method calculates the mean time between alarms.

This information is displayed under the heading "Alarm Weeks". Thus, for the pump #26, the mean time between alarms was 20.

The next column heading is "Wear Weeks" and it indicates the time interval between alerts that were caused by parameters associated with wear. Likewise, the next column entitled "Cont Weeks " indicates the mean time interval between alerts caused by parameters associated contamination, and the column entitled "Chem Weeks" provides the mean time interval between alerts caused by parameters associated with oil chemistry.

The display of the information as shown in FIG. 6 is quite useful to a predictive maintenance engineer. For example, by simply examining this information, the predictive maintenance personnel could set the sampling interval on each machine by simply dividing the third column by two. For example, the number one machine shows a mean time between alerts of 14. Thus, the sample interval for that machine should be 7 or less. The No. 2 motor, however, has a mean time between the alerts of 23. Thus, the sample interval for the No. 2 motor could be set at 11, which is less than one-half of 23. However, to further automate and simplify the process of setting the intervals for taking samples for each machine, the method of the present invention provides the option of having the program automatically suggest a sampling time interval for each machine.

To perform this task, each machine must first qualify by determining whether a sufficient number of samples have been taken to enable a suggestion. Preferably, to qualify a machine, the number of samples is divided by the number of points for each machine. Thus, for the No. 59 roll process, 38 samples divided by 2 sample points equals 19. If the threshold for making a suggestion is set at 15, the No. 59 roll process qualifies for a suggestion. The number in the column entitled "Sample Weeks" may be divided by two, and the answer would then be rounded down to the nearest whole number. Thus in the case of the number 59 roll process, a time interval of five would be suggested.

In the case of the number 64 machine tool spindle, the number of samples, 7, divided by the number of points, 3, gives an answer that is less than 15. In such case, a sample interval would not be suggested. Instead, it would indicate that insufficient samples have been collected to suggest a sample interval.

By providing the columns entitled "Wear Weeks, Cont Weeks, and Chem Weeks" information has been provided regarding the nature of the problem causing alerts. For example, the No. 18 engine has a mean time between alerts of 11 and a mean time between contamination alerts of 13. This information alone would suggest that contamination was a problem for the No. 18 engine. As another example, consider the number 21 engine. The mean time between alerts for contamination is six weeks, oil chemistry is 26 weeks, and wear is 63 weeks. This information would quickly indicate to predictive maintenance personnel that this engine has a problem with contamination, but it is exceptionally resilient in the wear category and does not have a problem in the oil chemistry category.

To further automate the process of analyzing the data, the method of the present invention identifies potential problems and brings them to the attention of the operator. For example, the computer identifies the top 10% of the machines having the shortest mean time between alerts and displays those machines separately along with all of their data and identifies them as potential problems. Likewise, for each category the computer identifies the top 10% of the machines having the shortest mean time between alerts in that category and displays all of the data for those machines as well as a suggestion that such a machine may have a problem associated with a particular category, such as wear, contamination, or oil chemistry. Thus, the operator has a new tool for organizing work. For example, when a plant is prepared to perform maintenance directed to correcting wear problems, the predictive maintenance engineer may make a query to identify the top 10% (or another percentage) of potential problem machines in the wear category based on the mean time between alerts in the wear category. Thus, preventative maintenance can be performed efficiently by doing the same type of preventative maintenance in a single session and those machines having the greatest need for a particular type of maintenance will receive that maintenance.

Thus, it will be appreciated that the calculation of the mean time between alerts and the categorization of the various types of mean times between alerts provides useful information for understanding the effectiveness of a predictive maintenance program, for setting intervals for conducting measurements or sampling the machines, and for organizing effective preventative maintenance programs.

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. A method for assisting a user in analyzing condition monitoring information from at least one device, the method comprising the steps of:

collecting a plurality of samples of condition monitoring data for one or more parameters over time for at least one device, wherein the condition monitoring data includes one or more parameter measurements;

identifying one or more parameters at warning status based on the plurality of samples, wherein a parameter is at warning status when the parameter measurement is the same as or greater than a predetermined warning limit;

determining a mean time between warnings for the at least one device, wherein the mean time between warnings for the at least one device is an average time between collections of samples where at least one parameter is at warning status; and displaying information comprising at least one of the mean time between warnings for the at least one device, a mean time between warnings for individual parameters, and a number of samples collected.

2. The method of claim 1, wherein the warning status is an alert status and the warning limit is an alert limit.

3. The method of claim 1, wherein the warning status is an alarm status and the warning limit is an alarm limit.

4. The method of claim 1, further comprising a step of identifying potentially faulty devices based on the devices having a smallest mean time between warnings.

5. The method of claim 1, further comprising a step of determining a frequency of maintenance for the at least one device based on the mean time between warnings for the at least one device.

6. The method of claim 5 wherein the frequency of maintenance is a percentage of the mean time between warnings for the at least one device.

7. The method of claim 5 wherein the frequency of maintenance is determined only for devices for which a sufficient number of samples has been collected.

8. The method of claim 1, wherein the displaying step includes displaying information comprising an overall average of the parameter measurements and averages of the parameter measurements for at least one period of time.

9. The method of claim 8 wherein the displayed averages are normalized averages.

10. The method of claim 8 wherein the displaying step comprises displaying a graphical representation of the averages of the parameter measurements for at least one period of time.

* * * * *